United States Patent
Stingl et al.

(10) Patent No.: US 7,172,588 B2
(45) Date of Patent: Feb. 6, 2007

(54) LASER DEVICE

(75) Inventors: Andreas Stingl, Korneuburg (AT); Ferenc Krausz, Vösendorf (AT)

(73) Assignee: Femtolasers Produktions GmbH (AT)

( * ) Notice: Subject to any disclaimer, the term of this patent is extended or adjusted under 35 U.S.C. 154(b) by 662 days.

(21) Appl. No.: 10/398,154

(22) PCT Filed: Oct. 2, 2001

(86) PCT No.: PCT/AT01/00309

§ 371 (c)(1), (2), (4) Date: Apr. 1, 2003

(87) PCT Pub. No.: WO02/28305

PCT Pub. Date: Apr. 11, 2002

(65) Prior Publication Data

US 2004/0102767 A1 May 27, 2004

(51) Int. Cl.
*A61B 18/20* (2006.01)
*A61C 1/00* (2006.01)
*H01S 3/10* (2006.01)

(52) U.S. Cl. .................. 606/10; 606/13; 433/29; 433/215; 372/18; 372/29.01; 372/98

(58) Field of Classification Search .............. 606/3, 606/10–14; 372/18, 19, 25, 26, 29.01, 29.011, 372/72, 92, 98; 433/29, 215
See application file for complete search history.

(56) References Cited

U.S. PATENT DOCUMENTS 4,375,684 A 3/1983 Everett (Continued)

FOREIGN PATENT DOCUMENTS

DE 9208617 9/1992

(Continued)

OTHER PUBLICATIONS

L. Turi, et al., "Diode-Pumped Nd:YLF All-In-One Laser", *Optics Letters*, vol. 20, No. 14, Jul. 15, 1995, pp. 1541-1543.

(Continued)

*Primary Examiner*—David M. Shay
(74) *Attorney, Agent, or Firm*—Ostrolenk, Faber, Gerb & Soffen, LLP (57) ABSTRACT

A dental laser arrangement switchable between different modes of operation, the arrangement including a laser device operable as a laser oscillator and as a laser amplifier. The laser device includes a laser resonator having a pump unit and an active modelocker as well as an optic loss element that introduces selective losses in the resonator. The laser arrangement further includes a laser beam-out-coupling unit. The modelocker is connected to a control circuit for switching between a CW-mode of operation for coagulating soft tissue, in which the modelocker is switched off, and two short-pulse modes of operation in which high frequency signals of equal frequencies, but different powers are applied by the control circuit to the modelocker so as to generate laser pulses of a pre-determined duration. One of the two short-pulse modes of operation is provided for ablation of hard tooth tissue, and the other short-pulse mode of operation, in which the laser radiation has a lower peak power in comparison with the first-mentioned short-pulse mode of operation, is for surface sealing of hard tooth tissue. An output of the control circuit furthermore is applied to the activatable optic loss element for controlling the losses in the resonator in the short-pulse modes of operation.

13 Claims, 8 Drawing Sheets

U.S. PATENT DOCUMENTS

| | | | |
|---|---|---|---|
| 4,521,194 A | 6/1985 | Myers et al. | |
| 4,725,787 A | 2/1988 | Chandra | |
| 5,742,634 A | 4/1998 | Rieger et al. | |
| 5,861,196 A | 1/1999 | Kuo et al. | |
| 6,122,097 A * | 9/2000 | Weston et al. | 372/72 |
| 6,162,213 A * | 12/2000 | Stewart | 606/10 |
| 6,414,980 B1 * | 7/2002 | Wang et al. | 372/92 |
| 6,482,199 B1 * | 11/2002 | Neev | 606/10 |

FOREIGN PATENT DOCUMENTS

| | | |
|---|---|---|
| EP | 0109254 | 5/1984 |
| EP | 0458681 | 11/1991 |
| EP | 0514898 | 11/1992 |
| EP | 0609978 | 8/1994 |
| EP | 0654251 | 5/1995 |
| JP | 8-255941 | 10/1996 |
| WO | 92/04871 | 4/1992 |
| WO | 95/32679 | 12/1995 |
| WO | 98/10494 | 3/1998 |
| WO | 98/41355 | 9/1998 |

OTHER PUBLICATIONS

A. Stingl, et al., "Generation of 11-fs Pulses from a Ti:Sapphire Laser Without the Use of Prisms", *Optics Letters*, vol. 19, No. 3, Feb. 1, 1994, pp. 204, 205 and 230.

* cited by examiner

FIG. 10

LASER DEVICE

BACKGROUND OF THE INVENTION

The invention relates to a dental laser arrangement switchable between different modes of operation.

Such a dental laser arrangement is already known from WO 98/41355 A (a similar laser arrangement is described in WO 95/32679 A); there, the laser radiation is used for the ablation of hard tooth tissue, and moreover, it is provided to have different laser radiation with different wave lengths for different applications (e.g. surface ablation and in-depth ablation) and, accordingly, different laser sources are to be employed between which it is switched during operation. This use of several laser sources as well as the further provided use—according to WO 98/41355 A—of separate optical fibers for each laser radiation is, however, rather complex.

As such, dental medicine has various possibilities of using lasers. For instance, in addition to the removal of tooth tissue, the sealing of surfaces of hard tissue by means of short laser pulses is conceivable, superheating of the tooth tissue having to be avoided just as during ablation thereof. On the other hand, thermal interactions between laser beam and tissue are conceivable and desired, i.e. in that case when a coagulation of protein is desired for the stopping of bleedings.

As has been mentioned, various laser sources have been used in the past for various treatments in dental medicine, wherein also the changing between these systems is complex, in particular when additional parts, such as manual devices, must be exchanged.

On the other hand, short-pulse laser arrangements are already known with which short laser pulses of high energy are produced in a mode-locked state. Such short-pulse laser arrangements are, e.g., used for the processing of materials or also for scientific projects, and also a use in dental medicine has already been suggested, cf. U.S. Pat. No. 5,742,634 A. As regards the production of short laser pulses, reference may also be made to WO 98/10494 A as well as to A. Stingl et al: Generation of 11-fs pulses from a Ti:sapphire laser without the use of prisms; Optics Letters Vol. 19, No. 3, 1 Feb. 1994, pp. 204–206.

The standard technique for producing short laser pulses of high energy is based on the technique of a laser oscillator and a laser amplifier. The laser oscillator which contains a pump unit to which, e.g., a laser pump beam is supplied, or in which a diode laser is provided, will generate a sequence of short laser pulses of low energy, e.g. with a repetition frequency in the range of some ten MHz. From these oscillator laser pulses, pulses with a lower repetition frequency are selected and amplified in a regenerative or so-called multi-pass amplifier to give pulses of high energy.

What is also known is the so-called "all-in-one" laser concept, in which merely one laser arrangement is provided which is used both as oscillator and also as regenerative amplifier, by simply performing the pulse formation (at low energies), on the one hand, and the amplification (to high energies), on the other hand, at different times. Known laser arrangements of this type (cf. e.g. L. Turi, T. Juhasz: Diode-pumped Nd:YLF all-in-one laser; Optics Letters Vol. 20, No. 14, 15 Jul. 1995, p. 1541–1543), having an oscillator function as well as an amplifier function use active modelocking with an acousto-optic modulator.

An all-in-one laser modified in relationship to the former is furthermore described in the earlier application WO 01/05001 A (PCT/AT00/00173) which is not a prior publication.

SUMMARY OF THE INVENTION

It is now an object of the invention to provide a dental laser arrangement of the initially defined type, with which a switching between the various modes of operation or types of treatment is possible in an advantageous manner, starting from a single laser system so that, e.g., during a dental treatment, an immediate switching is possible from one operation in which tooth tissue is removed, to an operation in which a bleeding can be stopped by protein coagulation and, optionally, also to an operation in which a sealing of open sites on a tooth is feasible. In particular, such a change-over should be enabled by a simple switching, e.g. by means of a mechanical switch.

Accordingly, the switchable dental laser arrangement of the invention is characterized in that a laser device capable of being operated as a laser oscillator and as a laser amplifier (all-in-one laser device) is provided, which comprises a laser resonator including a pump unit and an active modelocker as well as an optic loss element introducing selective losses in the resonator. The arrangement further comprises a laser beam-out-coupling unit. The modelocker is connected to a control circuit for switching between a CW-mode of operation for coagulating soft tissue, in which the modelocker is switched off, and two short-pulse modes of operation in which high frequency signals of equal frequencies, but different powers are applied by the control circuit to the modelocker so as to generate laser pulses of a pre-determined duration. One of the two short-pulse modes of operation is provided for removing hard tooth tissue, while the other short-pulse mode of operation, in which the laser radiation has a lower peak power in comparison with the first-mentioned short-pulse mode of operation, is for surface sealing of hard tooth tissue. Furthermore, an output of the control circuit is applied to the activatable optic loss element for controlling the losses in the resonator or in the short-pulse modes of operation.

The present dental laser arrangement thus is based on the previously described all-in-one concept, i.e. a single laser device is utilized which can be switched between the different modes of operation by means of the control circuit such that it either operates as a CW (CW—continuous wave) laser system, or as a short-pulse laser system where in turn different modes of operation are provided which also can be adjusted by means of the control circuit. In the CW mode of operation, a CW laser beam is generated with the modelocker turned off, i.e. no control signal is applied by the control circuit to the modelocker. The CW laser beam is defined as regards its output power, e.g. by a corresponding activation of the out-coupling. On the other hand, in the short-pulse modes of operation, an appropriate high-frequency signal with the required power is applied to the modelocker so as to generate the desired short pulses. Depending on the power of the respective high frequency signals applied to the modelocker, laser pulses of longer or shorter durations will form. In these short-pulse modes of operation, moreover the laser-amplifier-function is effected so as to be able to utilize, as initially described, individual short pulses after a build-up to high energies. In doing so, losses are temporarily introduced into the laser system which the pump unit attempts to equalize by continuously increasing the amplification. If then, at a high level of amplification, the losses are suddenly switched off, the short laser pulse is brought to a high energy within a few passes in the resonator as a consequence of the still high amplification in the pump unit, and then it is coupled out at the time of saturation. It is also particularly advantageous in this instance that the optic loss element is of multiple use, i.e. for the power control in the continuous wave operation, on the one hand, and as a control and switching element in the short-pulse modes of operation, on the other hand. The activatable optic loss element may simply be formed by an optic switch controlling the degree of out-coupling of the laser beam, in particular by a Pockels cell in combination with a λ/4-platelet. This optic switch or this Pockels cell, respectively, introduces losses in the laser radiation within a longer rhythm in that a part of the laser radiation (by an appropriate rotation of its plane of polarization) is out-coupled at a beam divider; when applying a λ/4 voltage signal to the Pockels cell in combination with the λ/4-platelet, or when switching off the voltage at the optic switch, respectively, avoiding of the out-coupling, or out-coupling of the short pulse at the desired point of time will be achieved as a consequence of the respective resultant orientation of the plane of polarization of the laser beam.

To produce the degree of out-coupling of the laser beam in a suitable manner, for the purpose of introducing losses or for amplifying the generated short pulses and out-coupling the same, it is advantageous if the control circuit is switchable to the Pockels cell to deliver voltages of different levels to the Pockels cell, depending on the mode of operation turned on. For the short-term build-up of the laser pulses in the amplifying phase (without out-coupling of the laser radiation), as well as the out-coupling of the energy-rich short pulses occurring at saturation, it is furthermore suitable if the control circuit is adapted for delivering separate voltage-ON and OFF-switching-signals to the Pockels cell. To carry out the different switching procedures in the correct phase, it is, moreover, advantageous if the ON- and OFF-switching-signals in the control circuit are derived from the high frequency signal supplied thereto by dividing the frequency and by means of different delaying elements.

The modelocker may, e.g., be an acousto-optic modelocker, and it will cause the generation of laser pulses of a frequency basically determined by the frequency of the high frequency signal, which frequency, of course, must be adapted to the length of the resonator and, for instance at customary resonator length (and thus, travel times of the laser pulses in the resonator) can amount to 75 or 80 MHz. On the other hand, in the short-pulse modes of operation, the amplified laser pulses that have been enriched in energy will occur at a repetition frequency of, e.g., 5 kHz.

In order to have laser radiation of different energies available in the different short-pulse modes of operation, the modelocker can be switched by the control circuit by means of high frequency signals of the same frequency, yet different power. Depending on the power of the high frequency signal applied to the mode-locker, short pulses of correspondingly shorter or longer pulse duration will form, and these short pulses will be amplified to higher or less high peak powers in a manner described hereinafter. This will be done without any further adjustment of the laser device itself. The average output power naturally will remain the same. For controlling the power of the high frequency signal it is suitable if the control circuit includes a high frequency generator with an output amplifier that is capable of being regulated.

To render switching over between the individual modes of operation as simple as possible, the control circuit may be connected to a mode-of-operation-selection switch, e.g. a foot-operated switch. Depending on the position of the selection switch, the control circuit will deliver the appropriate control signals to the different components of the laser device, such as, in particular, to the modelocker or to the optic switch so as to adjust the desired mode of operation. As mentioned before, in this manner the aforementioned CW laser radiation can be provided for a "coagulation" of soft tissue, or a short-pulse generation can be effected if in a mode of operation "ablation", a high frequency signal of appropriate power is applied to the modelocker so as to generate the desired short pulses. In a mode of operation "surface sealing", the power of the high frequency signal applied to the modelocker will be reduced such that laser pulses of longer duration will form, with the laser radiation having a lower peak power.

A coagulation effect is best achieved with a CW laser beam having a power of up to 3 W, wherein the position of the laser focus may remain fixed. For removing tooth tissues, as has been shown in tests, a pulse duration of less than 1 ps is used. On the other hand, for surface sealing procedures, pulse durations of approximately 100 ps are provided. Such a surface sealing will be used by the dentist to seal open sites of the teeth. For the ablation of tooth tissue, just as in surface sealing, a heating of the tooth is to be avoided, wherein in the treatment of caries temperature increases of more than 5° C. not only being painful, but also possibly causing irreversible damage of the pulpa. For this purpose, the laser beam or its focus, respectively, may be reciprocated on the tooth.

To control the laser beam to certain targets, it is furthermore, advantageous if a frequency doubling device for providing a visible beam of light is provided in the path of the out-coupled laser beam which doubles the frequency of a part of the laser beam. Moreover, for a selective weakening of the laser beam power, it is suitable if a controllable weakening means, e.g. a disk having parts of different reflectivity or a wedge formed of a filter material is arranged in the path of the out-coupled laser beam.

BRIEF DESCRIPTION OF THE DRAWINGS

In the following, the invention will be explained in more detail by way of preferred exemplary embodiments, to which, however, it shall not be restricted, and with reference to the drawings. In the drawings, in detail, FIG. 1 schematically shows a dental laser arrangement, wherein a handpiece and a tooth to be treated are only quite schematically illustrated;

FIG. 4, comprising

FIG. 6, comprising partial diagrams

DETAILED DESCRIPTION OF THE PREFERRED EMBODIMENTS

Figure 1:
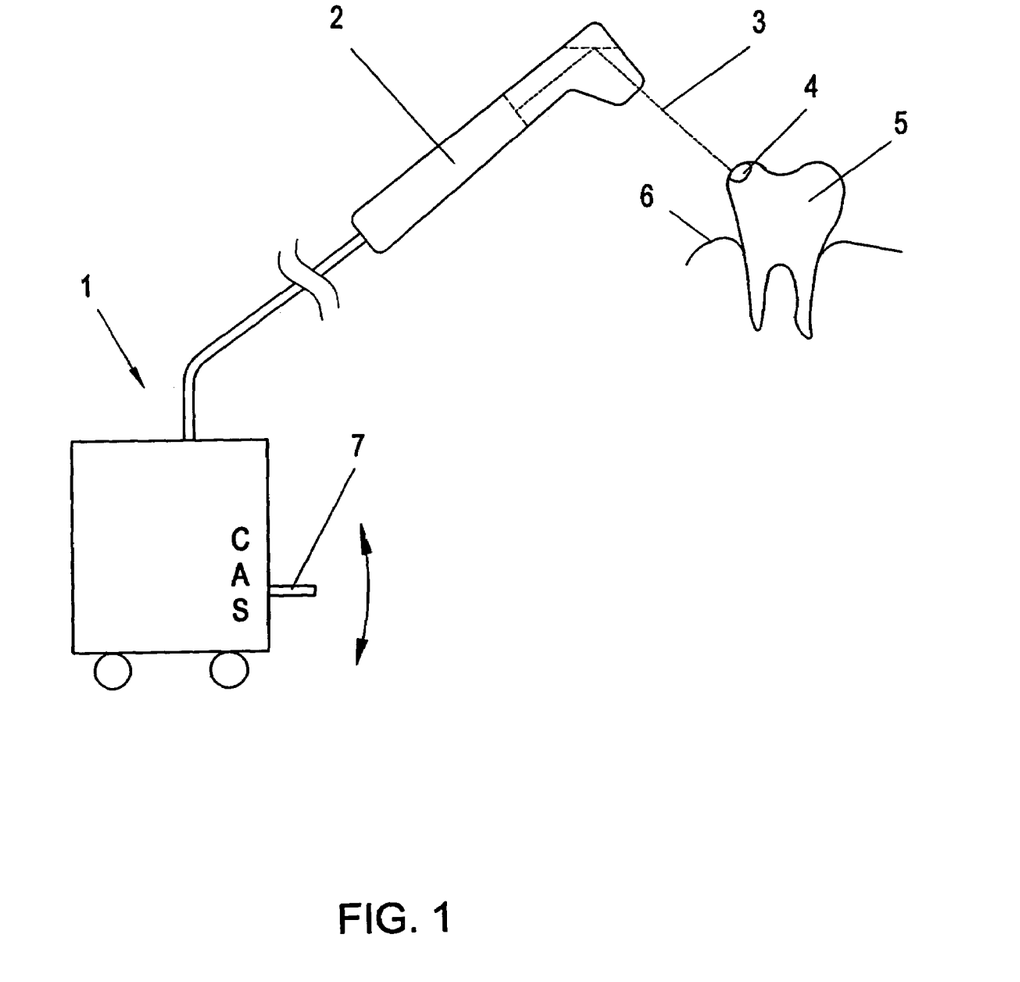

In FIG. 1, a dental-medical laser arrangement comprising a laser device 1 is illustrated merely quite schematic and not true to scale, to which a handpiece 2 is connected in a per se conventional manner, via articulated arms and the like (not illustrated), by means of which a therapeutic laser beam 3 is directed to the site 4 to be treated, located on a tooth 5. The site 4 to be treated may also be located in the region of the gingiva 6 if a bleeding is to be stopped there by the coagulation of protein.

The laser beam 3 is supplied from the laser arrangement 1 to the handpiece 2 via light conductors not further illustrated (cf. also pos. 22 in FIG. 2), as is known per se.

The laser device 1 comprises a foot-operated switch 7 which has, e.g., three positions corresponding to three modes of operation of the laser device 1, i.e. for (1) coagulating (mode C of operation); (2) ablation (mode A of operation); and (3) surface sealing (mode S of operation).

Figure 2:
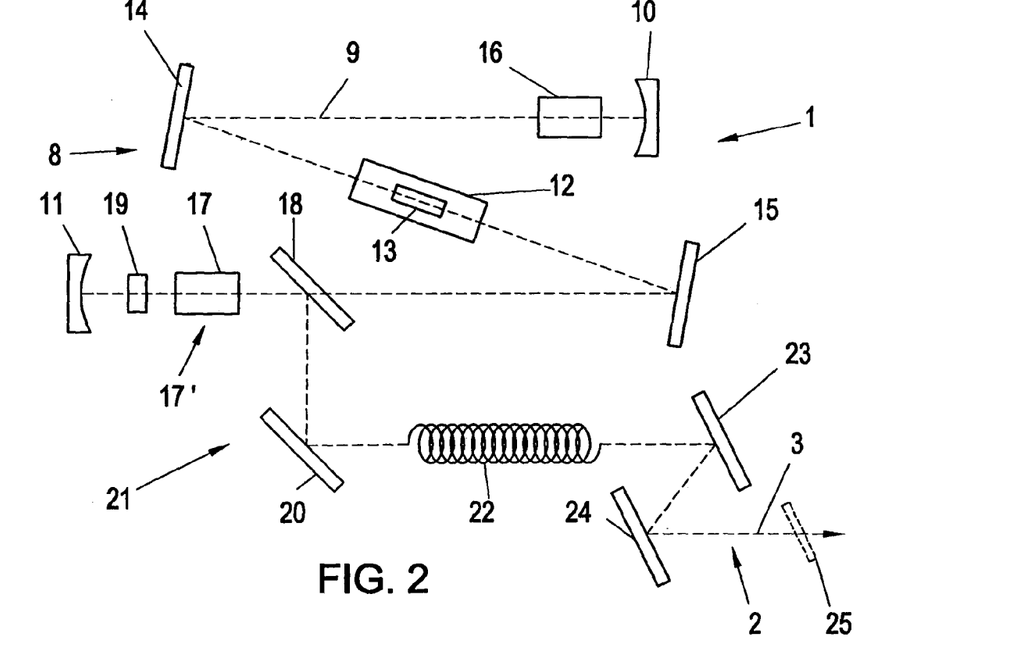
FIG. 2 shows a diagrammatic view of the all-in-one laser device and its individual optical components used therein.

In FIG. 2, the laser device 1 is illustrated in more detail as regards its optical components. The laser device 1 is constructed on the basis of an all-in-one laser, i.e. it serves as oscillator and as amplifier, a single resonator 8 being provided for generating the laser beam 9 in the resonator 8 in the respective mode of operation.

In detail, two resonator end mirrors 10, 11 are provided, with the laser beam 9 building up between them in the resonator 8 of the laser device 1. In the resonator 8, a pump unit 12 with an, e.g. diode-pumped, laser crystal 13 is contained which is merely schematically indicated and known per se; this pump unit 12 is arranged between two laser mirrors 14, 15 (in the manner of a Z-folding). Adjacent the one end mirror 10, moreover, an active modelocker 16, e.g. an acousto-optic modulator, is arranged which causes active mode-locking if activated accordingly, as will be explained in the following in more detail by way of FIGS. 3 to 6.

In the path of the laser beam 9, moreover, an optical switch, here in the form of a Pockels cell 17, is provided adjacent the other end mirror 11 of the resonator 8, losses being introduced in the laser beam by means of this optical switch or by this Pockels cell 17 in the short-pulse modes of operation A, S. This function as an optical loss element 17' is obtained by means of the Pockels cell 17, or in general, the optical switch, in that the laser beam 9 is out-coupled to various degrees, cf. the laser beam 3, wherein the degree of out-coupling here is controlled via the rotation of the plane of polarization of the laser beam 9 and, accordingly, the portions of the laser beam 9 which are allowed to pass on a polarization-dependent beam divider 18, or reflected, respectively. Accordingly, in a manner known per se, the Pockels cell 17 is selectively used as a polarization rotating means, and for out-coupling the laser radiation via the beam divider 18 by an appropriate rotation of the plane of polarization of the laser beam 9, furthermore, a λ/4 platelet 19 is provided in the radiation path of the laser beam 9, which platelet 19 causes a corresponding rotation of the plane of polarization of the laser beam 9 (a total of 90° at the λ/4 platelet 19 during a round trip of the laser beam 9). For the purpose of a—partial—out-coupling of the laser beam 9 on the beam divider 18 towards a mirror 20, the Pockels cell 17 is appropriately activated so as to cause the laser beam 9 to be reflected on the beam divider 18 to a higher or slighter degree by the rotation of the plane of polarization of the laser beam 9 effected on that Pockels cell (in addition to the rotation by the λ/4 platelet 19), as will be explained in the following in more detail by way of FIGS. 4 and 5. In this manner, an out-coupling unit generally denoted by 21 in FIG. 2 is realized.

The out-coupled laser beam 3 is supplied to the handpiece 2 via an optic fiber 22 as well as via two grids 23, 24 which cause a compression of the laser pulses. In the beam path past these two grids 23, 24, optical elements 25 may be provided so as to provide a visible pilot beam and/or a controllable weakening, as will be explained in the following in more detail by way of FIGS. 9 and 10.

Figure 3:
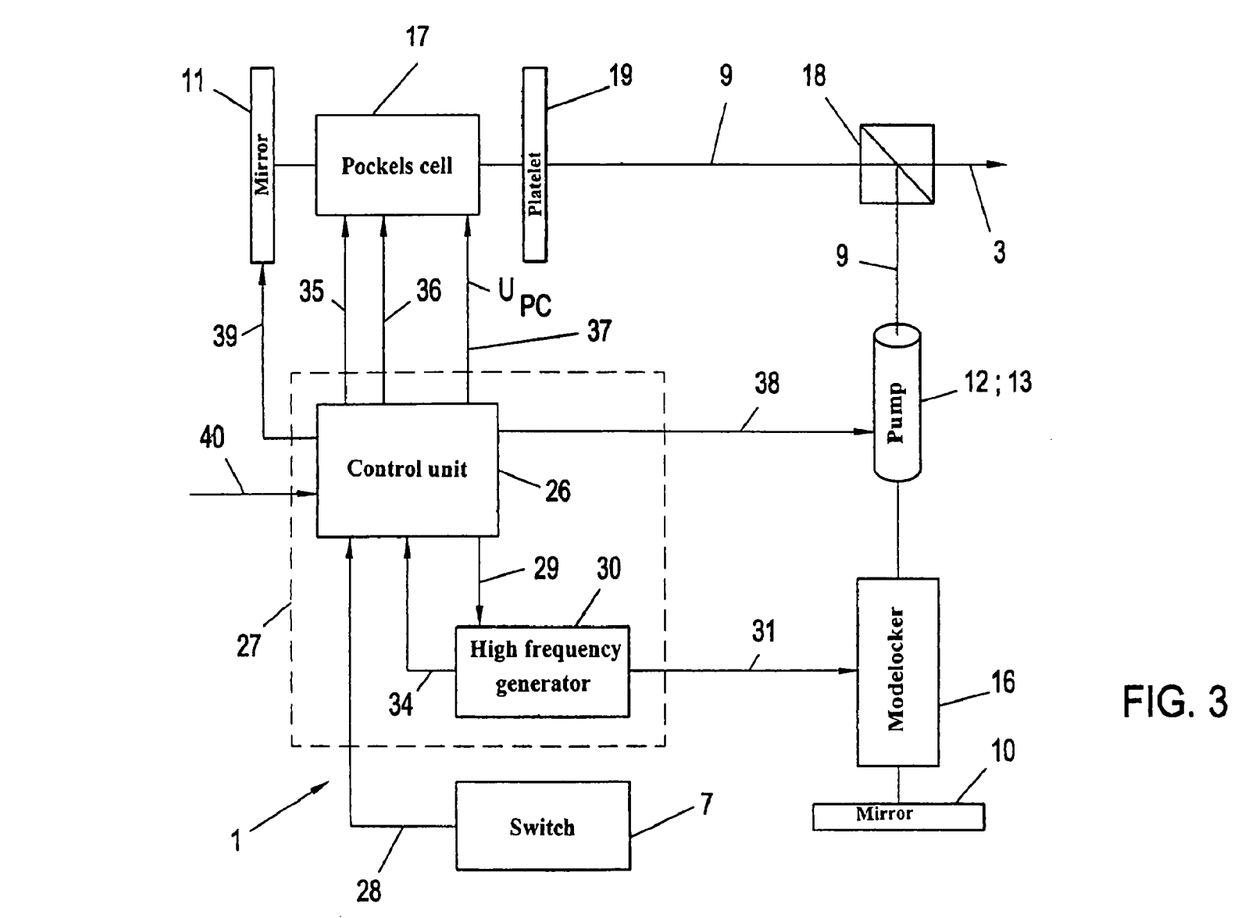
FIG. 3 shows a diagrammatic view of this laser device, with the individual components in the manner of a block diagram.

In FIG. 3, the aforementioned laser components are shown in a diagram that is somewhat simplified as compared to FIG. 2, and in addition, the associated electronic components are illustrated in the manner of a block diagram. In doing so, also the positions of the λ/4 platelet 19 and of the Pockels cell 17 have been exchanged so as to show that the relative positions of these two components 19, 17 are of no further relevance to obtain the desired out-coupling of the laser beam at the pre-selected point of time.

Figure 4A:
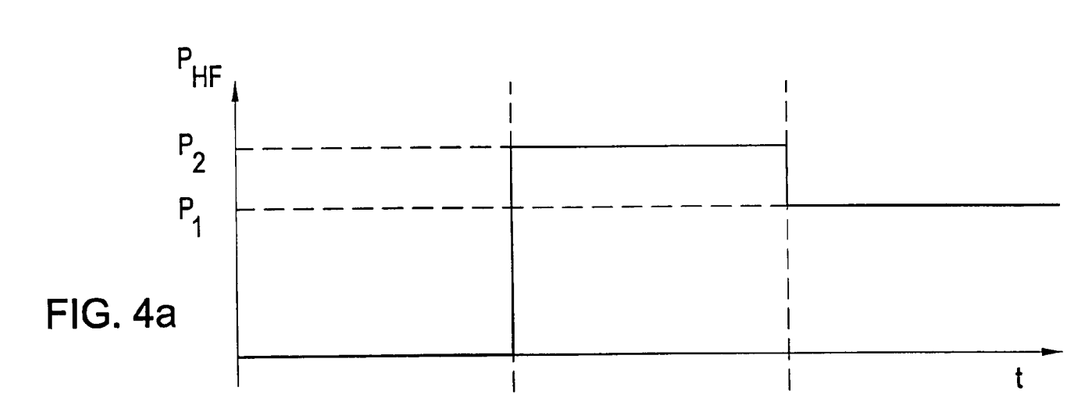
FIGS. 4a and 4b, shows a diagram with individual high frequency signal power levels (FIG. 4a) and control voltages (FIG. 4b) for the different modes of operation of the laser device.

The various components, such as in particular, the modelocker 16 and the Pockels cell 17, are electronically activated by a control unit 26 of an electric control circuit 27 which is connected to the foot-operated switch 7 for selecting the respective mode of operation (coagulation; ablation; sealing) via an input or control line 28. Then the control unit 26 will send a corresponding control signal via an output 29 to a high frequency generator 30, which will send either no signal at all, or one of two high frequency signals of different power levels $P_1$, or $P_2$, respectively (cf. FIG. 4a), via a line 31 to the modelocker 16. These two power levels $P_1$, $P_2$ are schematically shown in the diagram of FIG. 4a, wherein the high frequency signal of the higher power $P_{HF}=P_2$ will be delivered in the mode of operation "ablation", whereas the high frequency signal of the somewhat lower power $P_1$ will be delivered in the mode of operation "surface sealing". In the CW mode of operation "coagulating", no high frequency signal is applied to the modelocker 16, i.e. $P_{HF}=0$. In the lower part of FIG. 4, the mode of operation "coagulating" is shown at C, "ablation" at A, and "surface sealing" at S. For this purpose, the high frequency generator 30 may comprise an appropriate means to allow for a switching, or activating, respectively, in the region of its final stage (not shown in FIG. 3), as is per se conventional, and this is illustrated in FIG. 5, wherein the high frequency generator circuit 32 proper is followed by a controllable power amplifier 33 which, depending on the control signal at the input (line 29), will send to the modelocker 16 a high frequency signal of a power $P_2$ or of a power $P_1$ or no high frequency signal at all.

The high frequency signal generated by the high frequency generator 30 has the same frequency in the two short-pulse modes of operation, A, S, e.g. 75 MHz or 80 MHz, depending on the length of resonator 8, i.e. depending on the length of the paths of the laser pulses between the end mirrors 10, 11.

According to FIGS. 3 and 5, the control unit 26 furthermore receives a signal relating to phase information from the high frequency generator 30 on a line 34, as will be described in more detail hereinafter.

Figure 4B:
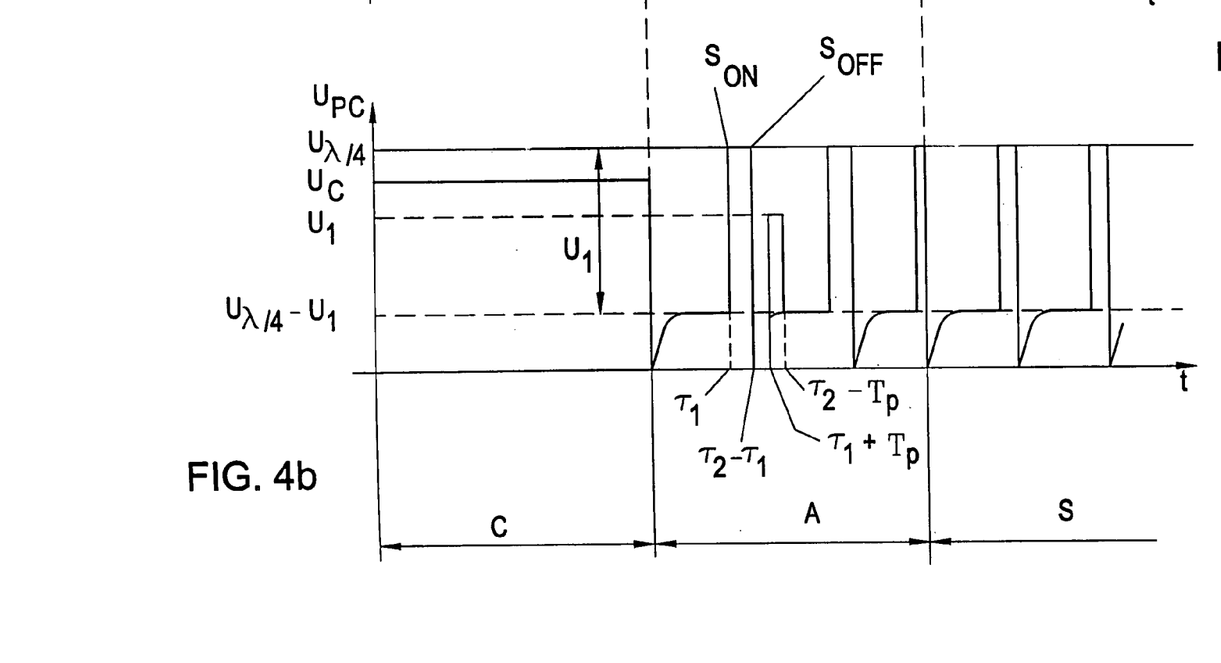
Figure 5:
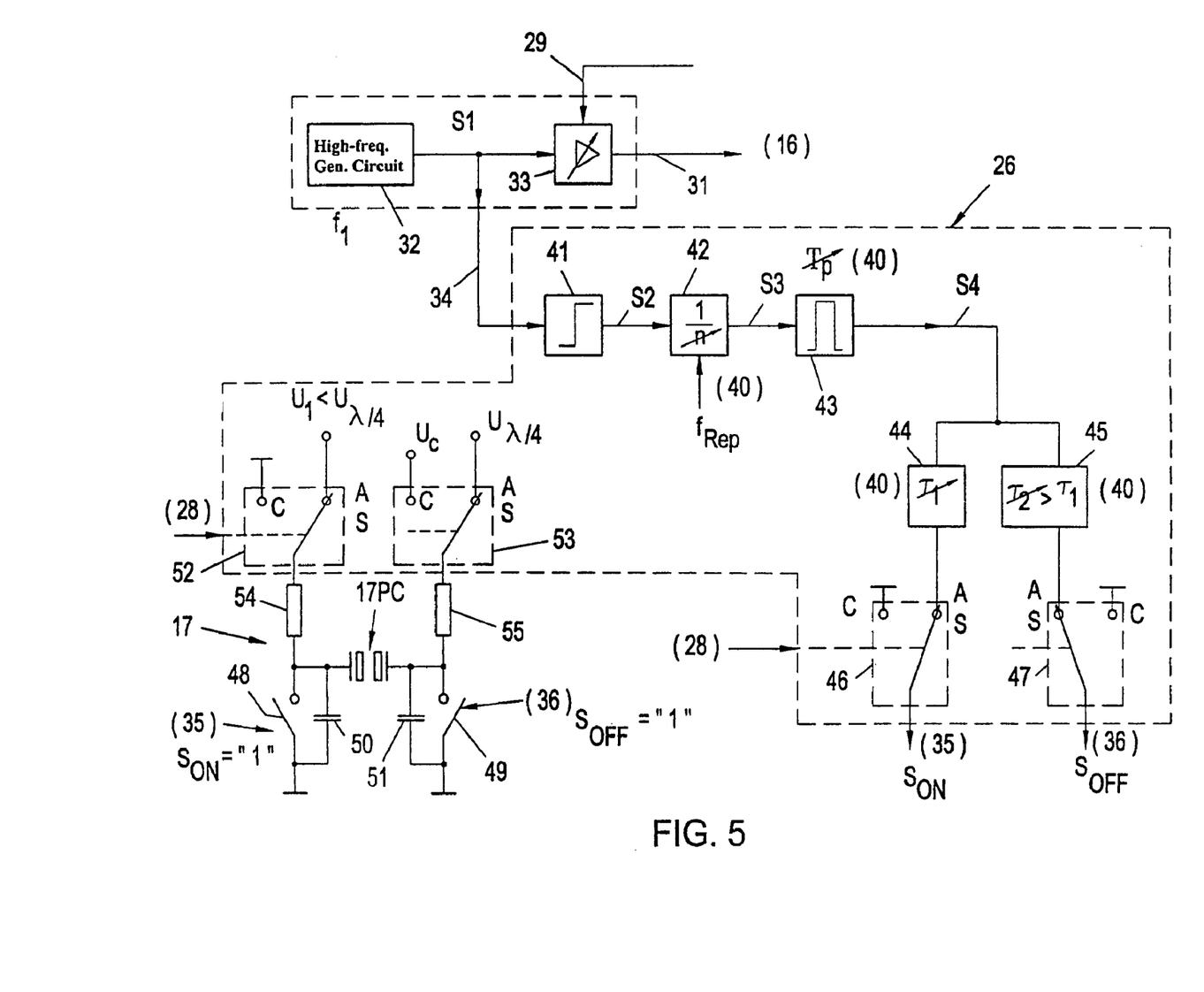
FIG. 5 shows a block diagram more detailed as compared to FIG. 3, of parts of the control components of the laser device.

The control unit 26, furthermore, activates the Pockels cell 17 via respective "off" and "on" control lines 35 and 36, respectively (cf. FIG. 3), and via a line 37, the required high voltage $U_{PC}$, e.g. the so-called λ/4 voltage $U_{λ/4}$ is applied to the Pockels cell 17 for a rotation of the plane of polarization of laser beam 9 by 90° at each round trip, cf. also FIG. 4b, so as to generate the desired amplified short pulses in the all-in-one laser device 1 during its operation as an amplifier, cf. also the following explanations given by way of FIGS. 5 and 6.

Via a line 38 to the pump unit 12 with the diode 13, the control unit 26 furthermore provides diode 13 with the required diode current, as is known per se. Moreover, the control unit 26 may be used to adjust the one resonator end mirror 11 via a control line 39, so as to precisely adjust the resonator length.

Via an input 40, time control parameters as well as set values regarding the repetition rate (pulse repetition frequency $f_{rep}$) can be supplied to the control unit 26.

In operation, in mode C of operation "coagulating", the modelocker 16 is turned off, i.e. no high frequency signal is supplied to it by the high frequency generator 30. The laser system operates in the low power region, wherein a CW laser beam 9 is generated which has a portion that is linearly polarized according to the polarizing beam divider 18 in the plane of drawing of FIG. 2. At Pockels cell 17, a voltage $U_{PC}=U_c$ (cf. FIG. 4) is applied which will range between 0 V and the λ/4 voltage $U_{λ/4}$. Here, the polarizing beam divider 18 will function as partially reflecting out-coupling means, wherein, depending on the level of voltage $U_c$ and thus on the amount of the rotation of the plane of polarization of the laser beam 9 by the Pockels cell 17 in combination with the rotation of polarization by the λ/4 platelet 19, e.g. 20% of the laser radiation will be coupled out. In detail, laser beam 9 will be allowed to pass by the beam divider 18 when it comes from the pump unit 12, and on its way returning from end mirror 11, it will partly be reflected by beam divider 18. As results from the previous discussion, the CW output will be adjusted by an appropriate selection of the voltage $U_{PC}=U_c$ applied to the Pockels cell 14—in accordance with the degree of coupling out. As has already been mentioned, in this mode C of operation "coagulating", the power suitably will be up to 3 W. In this mode C of operation, the out-coupled laser beam 3 will be focussed in a fixed focus at the site of treatment (4 in FIG. 1).

In the short-pulse modes of operation A and S (ablation, sealing), the mode-coupling means 16 of the laser apparatus 1 will be activated, a high frequency signal of a certain power, depending on the mode of operation (A, or S, respectively), being applied as indicated by the control circuit 27 or, more precisely, by its high frequency generator 30, to the modelocker 16 so as to generate short pulses having a duration of, e.g., approximately 1 ps (mode A of operation, "ablation"), or approximately 100 ps (mode S of operation, "sealing"), in correspondence to the high frequency power applied, $P_2$, or $P_1$, respectively.

From the series of short pulses generated with the frequency of the high frequency signal, individual pulses will be selected in the amplifying phase of the laser device 1, and amplified as they repeatedly pass through the resonator 8, as is known per se.

In detail, in this mode of operation of the laser device 1, losses are introduced in a first phase in that a larger portion of the laser radiation, i.e. 50–60%, are out-coupled from the resonator 8 by applying an appropriate voltage to Pockels cell 17. By this, a high amplification will of necessity be obtained in the laser crystal 13 of the pump unit 12 so as to compensate for these losses. The out-coupled laser radiation at the handpiece 2 is to be viewed merely as an inessential background of low energy.

As soon as a saturation has been reached, the λ/4 voltage $U_{λ/4}$ will be applied to Pockels cell 17, this being so at a time at which the laser pulse in resonator 8 according to FIG. 2 will be at the right-hand side of Pockels cell 17, such as when it is located in the region of the modelocker 16. By this, at the subsequent passage of the laser pulses towards the end mirror 11 and back, a total of twice a λ/2 rotation of the plane of polarization will be obtained so that out-coupling of the laser beam 9 will no longer occur. However, amplification in the pump unit 12 at this time is high, and the laser pulse will build up in terms of energy in 20 to 30 passages, with the amplification in pump unit 12, however, gradually decreasing at the same time so as reach a stationary state. At saturation, Pockels cell 17 will be turned off, i.e. a high voltage $U_{PC}$ will no longer be applied to it, and as a consequence of the rotation of the plane of polarization in the λ/4 platelet 19 only, a practically 100% out-coupling of laser beam 9 will now be effected on beam divider 18; the out-coupled laser pulse 3 is supplied to handpiece 2. Here, too, it holds again that the Pockels cell 17 will be turned off when, in the illustration in FIG. 2, the laser pulse is on the right-hand side of the Pockels cell in resonator 8.

A corresponding information on the location of the laser pulse (phase information) can be derived from the modelocker signal, since, e.g., in the maximum of the high frequency signal that is applied to the modelocker 16, the laser pulse is present in the modelocker 16. As has been mentioned before, this phase information regarding the position of the laser pulse is delivered from the high frequency generator 30 to control unit 26 via line 34.

In FIG. 5, an example for supplying switching pulses delivered by the control unit 26 via lines 35 ("ON") and 36 ("OFF") to the Pockels cell 17—in addition to the respective high voltage $U_{PC}$ via line 37—is illustrated in more detail. It can be seen that the high frequency signal $S_1$ generated by the high frequency generator circuit 32 and having frequency $F_1$ is branched off even before it is amplified in the power amplifier 33, and in parallel to the power amplifier 33 also is supplied to the control unit 26 as phase information signal via line 34, as illustrated in FIG. 5 by broken lines.

In the control unit 26, the high frequency signal $S_1$ (cf. also FIG. 6a) is supplied to a pulse former stage 41 so that a pulse signal $S_2$ (cf. FIG. 6b) with rectangular pulses will be obtained which is applied to an adjustable frequency divider 42 which is adjusted with a signal containing the repetition frequency $f_{rep}$ (via line 40, cf. also FIG. 3). Signal $S_3$ at the output of this frequency divider 42 (cf. FIG. 6c) accordingly has a period $T_R=1/f_{rep}$, in contrast to period $T_1=1/F_1$ of the high frequency signal $S_1$, or of the pulse signal $S_2$, respectively. Then pulse signal $S_3$ is applied to a monoflop 43 which produces pulses of a given, adjustable pulse duration $T_P$. This pulse, i.e. signal $S_4$ (illustrated in FIG. 6d) will then be applied to two delay members 44 and 45, respectively, connected in parallel to each other, a time delay $τ_1$ (delay member 44), or $τ_2>τ_1$, respectively, (delay member 45) which each is adjustable, being introduced. In the short pulse modes of operation A and S, respectively, the thus delayed pulses $S_4$ will be obtained as "ON" switching signals $S_{ON}$ or "OFF" switching signal $S_{OFF}$ for the Pockels cell 17 via switches 46 and 47, respectively, schematically illustrated in FIG. 5—adjusted with the aid of the foot-operated switch 7 via line 28. In mode C of operation (coagulating), the switches 46, 47 are brought into a different switching position so that ground potential will be found at the outputs.

In the left-hand part of FIG. 5, the Pockels cell 17 including the Pockels cell crystal 17PC is shown the two connections of which are located on one switch 48 and 49 each: each one of these switches 48, 49 has a capacitor 50, or 51, respectively, connected in parallel therewith. Switch 48 is closed, if the "ON" switching signal $S_{ON}$ (cf. FIG. 6e) is high ("1"); on the other hand, switch 49 will be closed if the "OFF"—switching signal $S_{OFF}$ ("1") is supplied, i.e. is high (cf. FIG. 6f). As mentioned before, these switching signals are supplied via lines 35 and 36, respectively, in FIG. 3 and will be present at switches 46, 47 of control unit 26.

Furthermore, within the control unit 26, there exist three DC voltages, i.e. the λ/4 voltage $U_{\lambda/4}$, the—comparatively—somewhat lower voltage $U_c$ for the operational mode coagulating (mode C of operation) and a voltage $U_1$ which likewise is lower than the λ/4 voltage $U_{\lambda/4}$, cf. FIG. 4b in addition to FIG. 5. Furthermore, there is a connection to ground to which the (FIG. 5) left-hand side of the Pockels cell 17 is connected in the mode C of operation (coagulating). In this mode C of operation, the right-hand side of the Pockels cell 17 is connected to voltage $U_c$. For switching over to the short pulse modes of operation A, S, the switches 52, 53 are activated, which are merely schematically shown in FIG. 5, and which may be realized in conventional manner by electronic switches. Activation again is effected from the foot-operated switch 7 via the control line 28, cf. FIG. 3. In the short-pulse modes of operation A, S, the right-hand side of the Pockels cell 17 (according to the illustration in FIG. 5) is connected to the λ/4 voltage $U_{\lambda/4}$, whereas the left-hand side is connected to voltage $U_1$ via switch 52. The two voltages $U_1$ and $U_{\lambda/4}$ are applied via resistors 54 and 55, respectively.

Figure 6A:
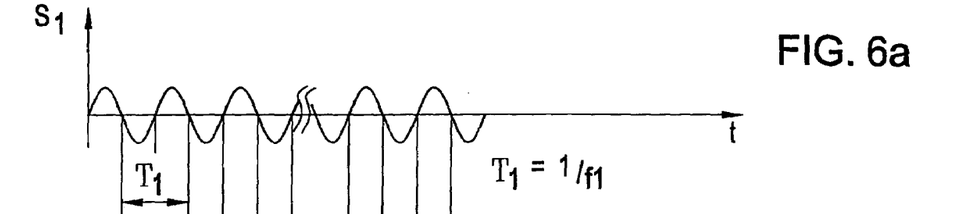
FIGS. 6a to 6f, shows the generation of various signals by means of the components of FIG. 5.
Figure 6B:
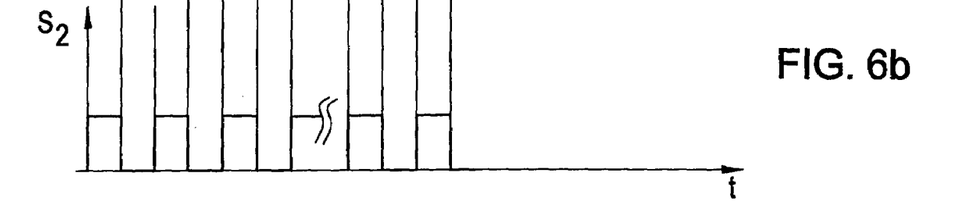
Figure 6C:
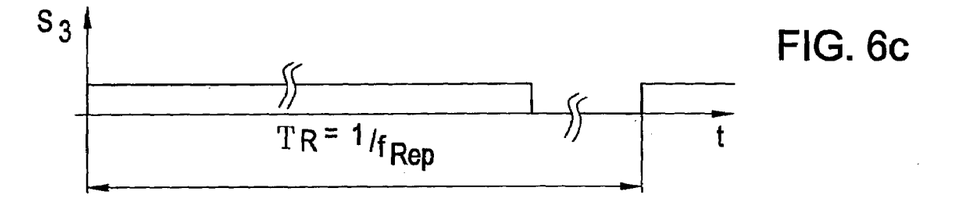
Figure 6D:
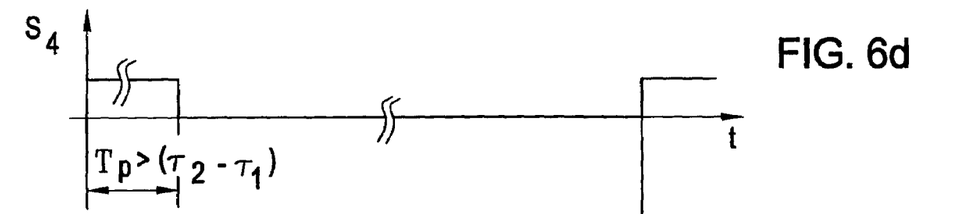
Figure 6E:
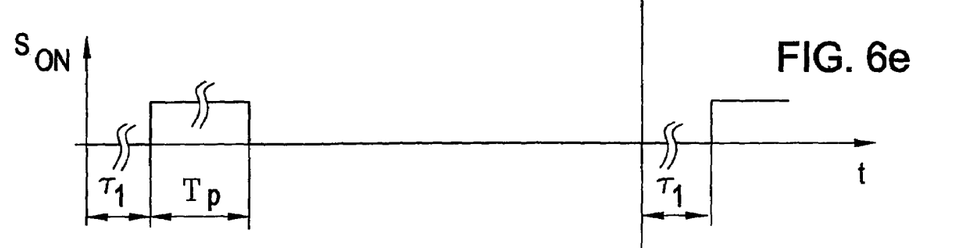
Figure 6F:
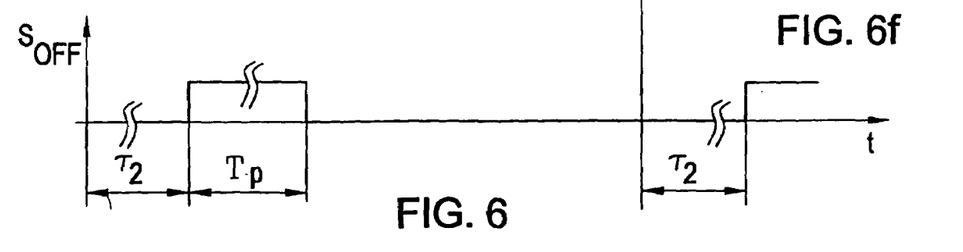

Now, if switch 48 (which, just like switch 49 and also switches 46, 47 could, of course, also be realized by electronic switches) is closed when an "ON" switching signal $S_{ON}$ is present (i.e., when pulse $S_{ON}$ according to FIG. 6e is at "1"), the current flow through the Pockels cell crystal 17PC is from the connection $U_{\lambda/4}$ via resistor 55, the Pockels cell crystal 17PC, to ground. If then after the period of time $\tau_2-\tau_1$ (cf. FIGS. 6d, 6e and 6f), the "OFF" switching signal $S_{OFF}$ changes to "1", the switch 49 will be closed so that both sides of the Pockels cell crystal 17PC are connected to ground via switches 48, 49. Current will then flow from the terminals exhibiting voltages $U_1$ and $U_{\lambda/4}$, respectively, via switches 52 and 53, respectively, and the series resistors 54 and 55, respectively, to ground without activation of the Pockels cell crystal 17PC. As a consequence, there will be no rotation of the plane of polarization of the laser beam 9 in resonator 8 by the Pockels cell 17 at this point of time, but merely by the λ/4 platelet 19, as mentioned before.

If then at the point of time $\tau_1+T_P$ (cf. FIG. 6e), the "ON" switching signal $S_{ON}$ returns to "0", cf. FIG. 6e, switch 48 will be opened again, while switch 49 will still stay closed for the remaining time in which the "OFF" switching signal $S_{OFF}$ is at "1". During this period of time, there will be a current flow from the terminal conducting voltage $U_1$ via switch 52, the resistor 54 and the Pockels cell crystal 17PC as well as the closed switch 49 to ground, i.e., laser beam 9 will be rotated in its plane of polarization according to the applied Pockels cell voltage $U_{PC}=U_1$, and losses will again be introduced in the laser resonator 8. If the OFF switching signal $S_{OFF}$ then also goes to "0" (point of time $\tau_2+T_P$ according to the illustration in FIG. 6f), also the switch 49 in FIG. 5 will be opened, and the Pockels cell 17, via switches 52, 53 and the resistors 54, 55, will then be at the difference voltage $U_{\lambda/4}-U_1$. Accordingly, also during this period of time—until the next switch-on signal $S_{ON}="1"$—a voltage ($U_{\tau/4}-U_1$) will be applied to Pockels cell 17, which voltage will cause a corresponding rotation of the plane of polarization of the laser beam 9 and, thus, coupling out of laser beam 9 via the beam divider 18. This procedure is schematically illustrated in FIG. 4b only during an amplifying period, while the remaining periods are illustrated in a simplified manner.

Figure 7:
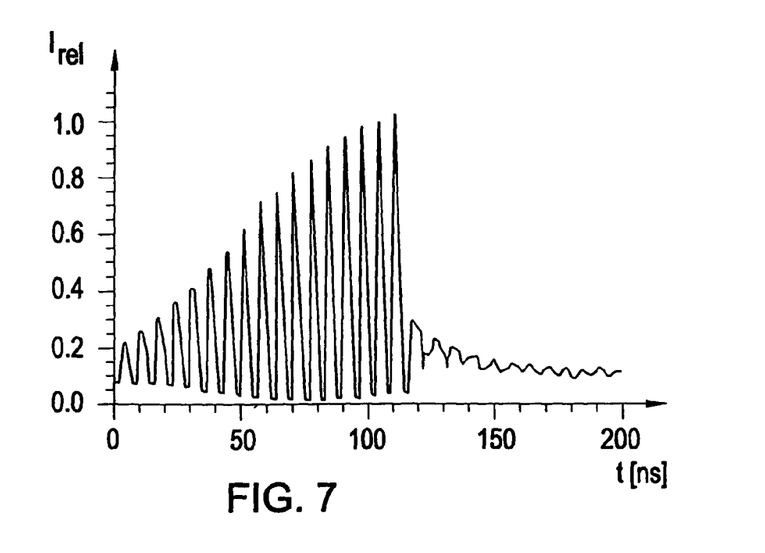
FIG. 7 shows a diagram to illustrate the procedure when amplifying the laser pulses.

As has been mentioned, during the times illustrated in FIG. 4b, where $U_{\lambda/4}$ is applied to the Pockels cell 17 (time interval $\tau_2-\tau_1$), an out-coupling of laser beam 9 is prevented, and during this time the laser pulse, as has been mentioned, will be substantially amplified in resonator 8 in 20 to 30 passages; this may also be seen in FIG. 7, in which this increase in the pulse energy is shown in the left half of the diagram, where the intensity $I_{rel}$ is applied over time. The duration $\tau_2-\tau_1$ is given by the time in which a saturation of amplification occurs.

If the voltage at Pockels cell 17 then goes to "0", the laser pulse will be coupled out of the resonator 8 by practically 100%, and supplied to handpiece 2.

The spectrum of the out-coupled laser pulse which has been amplified to a high peak power is widened by phase automodulation in optical fiber line 22 so as to shorten the pulse duration. The two grids 23, 24 (or mirrors, prisms, cf. FIG. 2) compress the pulse to the desired duration (<1 ps in the case of mode A of operation).

In the handpiece 2, a rapid movement of the laser focus which is not further illustrated and does not form part of the present invention, can be provided so as to avoid superheating at the treatment site 4. In mode S of operation ("surface sealing"), a high frequency signal is applied to the modelocker 16 which is of smaller power $P_1$ than in mode A of operation ("ablation"), in which the power $P_2>P_1$ is provided. In this manner, in mode S of operation, a longer pulse duration of the laser pulses is obtained than in mode A of operation. By an appropriate adjustment of the power $P_{HF}=P_1$ of the high frequency signal, a pulse duration of approximately 100 ps can be obtained in mode S of operation, whereas in mode A of operation, as has been mentioned, the pulse duration is in the order of 1 ps and therebelow.

Figure 8:
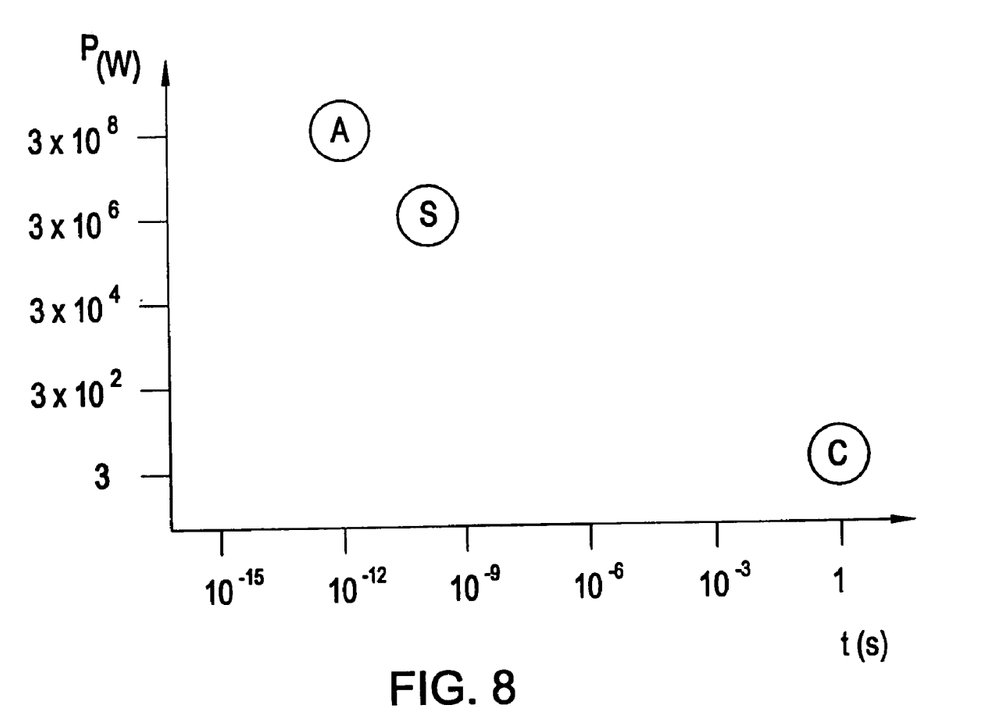
FIG. 8 shows a diagrammatic view for illustrating the fields of use for the different modes of operation of the laser device in a diagram "peak power" over "exposure time"

In FIG. 8, in a diagram the peak power P(W) over the active time t(s) in the three modes of operation A, S and C is schematically illustrated. Therein, it is visible that the peak power in mode A of operation, "ablation", is the highest, approximately in the order of $3 \cdot 10^8$ W. With a pulse duration <1 ps, this will mean the application of a pulse energy of approximately 300 μJ. In mode S of operation, "surface sealing", a pulse energy of 300 μJ will be applied with a pulse duration of approximately 100 ps—corresponding to a peak power of $3 \cdot 10^6$ W.

In the low power mode of operation C, "coagulating", a CW power of approximately 3 W will be applied for a few seconds.

With the aid of the foot-operated switch 7, a comfortable switching between the three modes of operation C, A and S is feasible.

In many applications in dental treatment, it is advantageous to provide a visible pilot laser beam, since then the out-coupled treatment laser beam 3 can more readily be directed to the correct treatment site 4. To produce the pilot laser, a visible laser beam can be derived from the therapeutic laser 3 by doubling the frequency, or an additional laser source, e.g. a conventional laser diode, may be employed whose visible laser beam is coupled in on a mirror (cf. the optic element 25 in FIG. 2).

Figure 9:
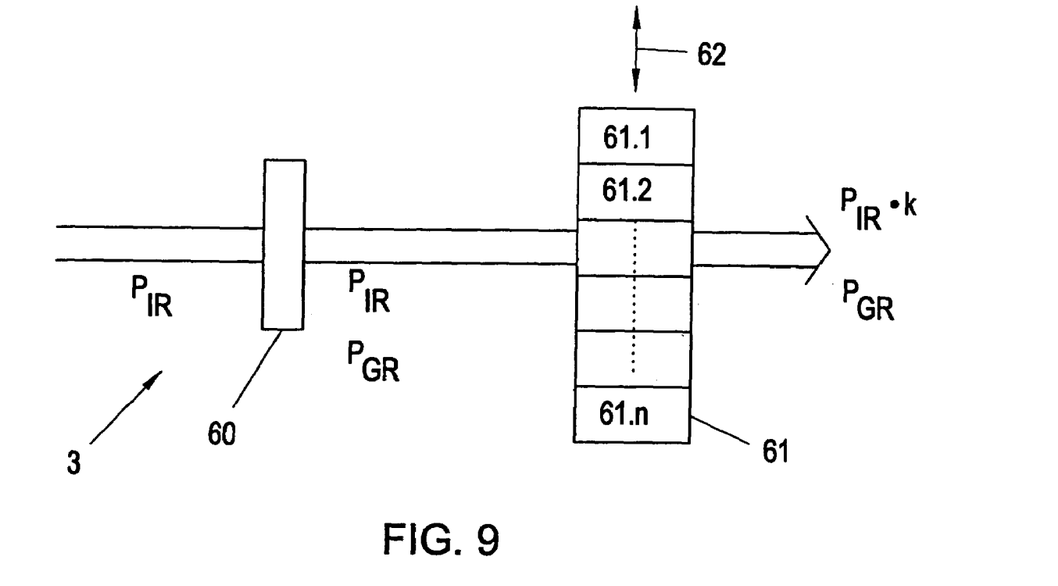
FIGS. 9 and 10 each show schematically the arrangement of a frequency doubling device and a controllable weakening means in the path of the out-coupled laser beam to additionally provide a pilot laser beam with visible light for rendering the target point visible as well as the possibility of providing a weakening of the laser beam power.
Figure 10:
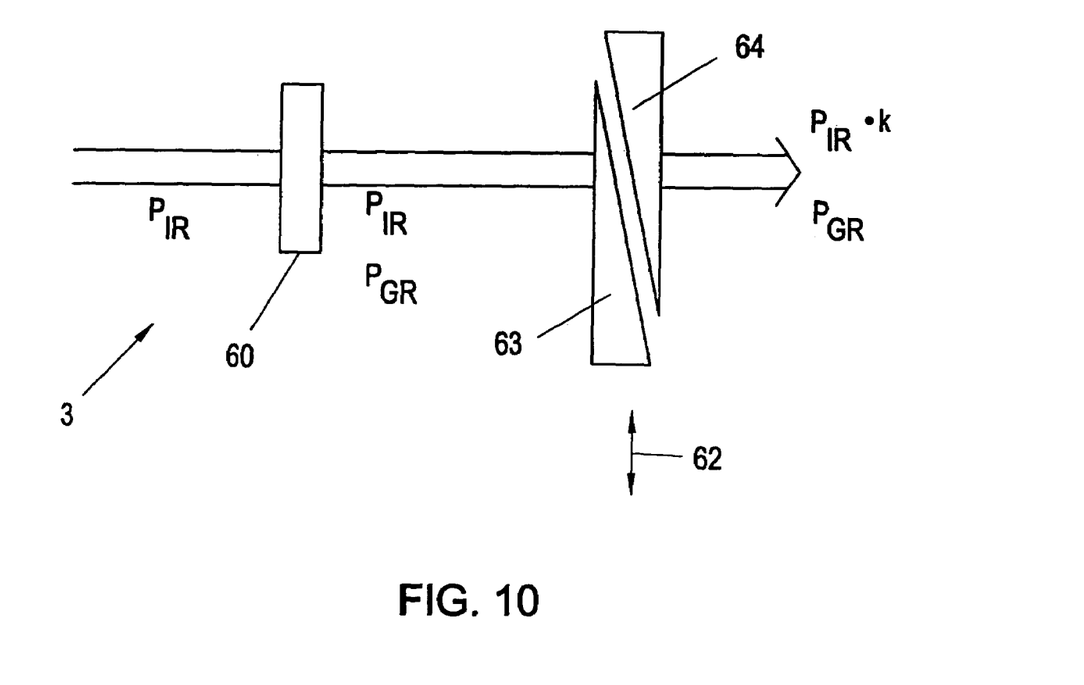

More in detail, the visible pilot laser beam preferably is derived from the treatment laser beam 3 by doubling its frequency, as is shown in FIGS. 9 and 10. The laser device 1 (cf. FIGS. 2, 3) operates at a fixed working point and continuously delivers the optic power $P_{IR}$. A small part of the output power which is in the infrared range (e.g. at 1064 nm) will be doubled in frequency by means of a non-linear crystal 60, and thus will be shifted to the green spectral range, cf. the note to "$P_{GR}$" in FIGS. 9 and 10. Since only approximately 1% of the radiation has to be converted so as to generate a pilot beam of good visibility, the infrared(IR)-output power $P_{IR}$ will practically remain unchanged.

There are various ways which allow for a further lowering of the IR power without changing the pilot beam. According to FIG. 9, a disc 61 is used which is assembled of individual parts 61.1, 61.2 . . . 61.$n$, and which is shifted perpendicularly to the beam path, cf. arrow 62 in FIG. 9. The individual parts 61.1 . . . 61.$n$ each consist of a substrate coated with dielectric multi-layers whose properties can be freely adjusted within a wide range in a manner known per se, by an appropriate selection of layer thicknesses and material. All the layers have in common that they are highly transparent for the green wave length (e.g. 532 nm); however, the reflectivity R for the IR beam will increase from layer to layer. The number of layers will determine how finely the power $P_{IR}$ can be varied. For instance, with six layers, the following decreases (factor k) can be provided:

layer 61.1: R=0 (k=1)
layer 61.2: R=20% (k=0.8)
layer 61.3: R=40% (k=0.6)
layer 61.4: R=60% (k=0.4)
layer 61.5: R=80% (k=0.2)
layer 61.6: R=100% (k=0)

According to FIG. 10, a wedge 63 consisting of a doped filter material is shifted perpendicularly to beam 3, cf. arrow 62. The filter material is selected such that the green pilot beam is hardly influenced, the IR beam, however, will be decreased depending on the thickness of wedge 63 (weakening factor k). At the tip of wedge 63, therefore, nearly the entire IR power will be transmitted (k=1), at the base it will be nearly completely absorbed (k=0). A second, undoped wedge 64 will correct the angle dispersion introduced therein.

The invention claimed is:

1. A dental laser arrangement switchable between different modes of operation, comprising: a laser device operable as a laser oscillator and as a laser amplifier, the laser device including a laser resonator having a pump unit for generating a laser beam, an active modelocker, and an actuatable optic loss element operatively arranged to introduce selective losses in the resonator; and a laser beam-out-coupling unit, the laser device further including a control circuit connected to the modelocker and operative to switch between a CW-mode of operation (C) for coagulating soft tissue, in which the modelocker is switched off, and two short-pulse modes of operation (A, S) in which high frequency signals of equal frequencies, but different powers are applied by the control circuit to the modelocker so as to generate laser pulses of a pre-determined duration, a first one of the two short-pulse modes of operation (A) being provided for ablation of hard tooth tissue, while a second of the short-pulse modes of operation (S), in which the laser radiation has a lower peak power in comparison with the first short-pulse mode of operation, is provided for surface sealing of hard tooth tissue, the control circuit having an output applied to the activatable optic loss element for controlling the losses in the resonator in the short-pulse modes of operation.

2. A dental laser arrangement according to claim 1, wherein the activatable optic loss element is an optic switch arranged to control a degree of out-coupling of the laser beam.

3. A dental laser arrangement according to claim 1, wherein the controllable optic loss element is a Pockels cell in combination with a λ/4 platelet.

4. A dental laser arrangement according to claim 3, wherein the control circuit is configured to be switchable to deliver voltages of different level to the Pockels cell, depending on the mode of operation switched on.

5. A dental laser arrangement according to claim 4, wherein the control circuit is adapted for delivering separate voltage-ON and OFF-signals ($S_{ON}$, $S_{OFF}$) to the Pockels cell.

6. A dental laser arrangement according to claim 5, and further comprising delaying elements, the voltage-ON and OFF switching signals ($S_{ON}$, $S_{OFF}$) in the control circuit are derived from a high frequency signal ($S_1$) supplied to the control circuit by dividing the frequency and by delaying the then obtained signals in delaying elements for different delay times.

7. A dental laser arrangement according to claim 1, wherein the control circuit includes a high frequency generator with an output amplifier that is regulatable.

8. A dental laser arrangement according to claim 1, wherein the laser device includes a mode-of-operation-selection switch connected to the control circuit, the switch being operatively provided to select a mode of operation of the laser device.

9. A dental laser arrangement according to claim 2, and further comprising a frequency doubling device operatively arranged to provide a visible beam of light in a path of the out-coupled laser beam so as to double the frequency of a part of the laser beam.

10. A dental laser arrangement according to claim 2, and further comprising a controllable weakening member arranged in the path of the out-coupled laser beam.

11. A dental laser arrangement according to claim 8, wherein the mode-of-operation-selection switch is a foot-operated switch.

12. A dental laser arrangement according to claim 10, wherein the controllable weakening member is a disk having disk parts of different reflectivity.

13. A dental laser arrangement according to claim 10, wherein the controllable weakening member is a wedge formed of a filter material.

* * * * *

UNITED STATES PATENT AND TRADEMARK OFFICE
CERTIFICATE OF CORRECTION

PATENT NO.         : 7,172,588 B2                                      Page 1 of 1
APPLICATION NO. : 10/398154
DATED              : February 6, 2007
INVENTOR(S)        : Andreas Stingl and Ferenc Krausz It is certified that error appears in the above-identified patent and that said Letters Patent is hereby corrected as shown below:

Item (30) Foreign Application Priority Data Please Insert;
        October 2, 2000  [AT]  Austria    A1667/2000

Signed and Sealed this

Fifth Day of June, 2007

JON W. DUDAS
*Director of the United States Patent and Trademark Office*